(12) United States Patent
Dinh et al.

(10) Patent No.: US 7,699,832 B2
(45) Date of Patent: Apr. 20, 2010

(54) MEDICAL DEVICE HAVING A SURFACE INCLUDING A BIOLOGICALLY ACTIVE AGENT THEREIN, AND METHODS

(75) Inventors: Thomas Q Dinh, Minnetonka, MN (US); Rodolfo Padua, Richfield, MN (US); Jesus Casas-Bejar, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 704 days.

(21) Appl. No.: 11/138,545

(22) Filed: May 26, 2005

(65) Prior Publication Data

US 2005/0271696 A1 Dec. 8, 2005

Related U.S. Application Data

(60) Provisional application No. 60/574,739, filed on May 27, 2004.

(51) Int. Cl.
*A61K 9/22* (2006.01)
*A61F 2/00* (2006.01)

(52) U.S. Cl. .................................. 604/890.1; 424/426

(58) Field of Classification Search ....................... None
See application file for complete search history.

(56) References Cited

U.S. PATENT DOCUMENTS

| | | | |
|---|---|---|---|
| 4,224,177 A | 9/1980 | Macedo et al. | |
| 5,165,952 A | 11/1992 | Solomon et al. | |
| 5,281,419 A | 1/1994 | Tuan et al. | |
| 5,328,698 A | 7/1994 | Onwumere et al. | |
| 5,464,650 A | 11/1995 | Berg et al. | |
| 5,510,077 A | 4/1996 | Dinh et al. | |
| 5,554,182 A | 9/1996 | Dinh et al. | |
| 5,571,166 A | 11/1996 | Dinh et al. | |
| 5,591,227 A | 1/1997 | Dinh et al. | |
| 5,599,352 A | 2/1997 | Dinh et al. | |
| 5,624,411 A | 4/1997 | Tuch | |
| 5,628,785 A | 5/1997 | Schwartz et al. | |
| 5,679,400 A | 10/1997 | Tuch | |
| 5,697,967 A | 12/1997 | Dinh et al. | |
| 5,824,048 A | 10/1998 | Tuch | |
| 5,830,879 A | 11/1998 | Isner | |
| 6,013,099 A | 1/2000 | Dinh et al. | |
| 6,045,777 A | 4/2000 | Church et al. | |
| 6,106,454 A | 8/2000 | Berg et al. | |
| 6,187,370 B1 | 2/2001 | Dinh et al. | |
| 6,197,013 B1 | 3/2001 | Reed et al. | |
| 6,203,536 B1 | 3/2001 | Berg et al. | |
| 6,206,914 B1 | 3/2001 | Soykan et al. | |
| 6,228,845 B1 | 5/2001 | Donovan et al. | |
| 6,262,034 B1 | 7/2001 | Mathiowitz et al. | |
| 6,387,121 B1 | 5/2002 | Alt | |
| 6,395,029 B1 | 5/2002 | Levy | |
| 6,399,144 B2 | 6/2002 | Dinh et al. | |
| 6,652,581 B1 * | 11/2003 | Ding | 623/1.39 |
| 6,890,699 B2 * | 5/2005 | Seibold et al. | 430/270.1 |
| 7,077,859 B2 * | 7/2006 | Sirhan et al. | 623/1.15 |
| 2001/0002435 A1 | 5/2001 | Berg et al. | |
| 2002/0028243 A1 | 3/2002 | Masters | |
| 2002/0037358 A1 | 3/2002 | Barry et al. | |
| 2002/0082679 A1 | 6/2002 | Sirhan et al. | |

FOREIGN PATENT DOCUMENTS

WO WO 00/01322 1/2000

OTHER PUBLICATIONS

Gunnatillake et al., European Cells and Materials, 2003, 5: 1-16.*
Wan et al., J Microencapsul, 1992, 9: 53-62.*
Feldman, et al., Stent-Based Gene Therapy, J. of Long-Term Effects of Medical Implants, 10(1&2):47-68, 2000.
Klugherz, et al., Gene Delivery to Pig Coronary Arteries from Stents Carrying Antibody-Tethered Adenovirus, Human Gene Therapy, 13:443-454, 2002.
Klugherz, et al., Gene Delivery from a DNA Controlled-Release Stent in Porcine Coronary Arteries, Nature Biotechnology, 18:1181-1184, 2000.
Panetta, et al., A Tissue-Engineered Stent for Cell-Based Vascular Gene Transfer, Human Gene Therapy, 13:433-441, 2002.
Feldman et al., "Stent-Based Gene Therapy," *Journal of Long-Term Effects of Medical Implants*, 2000;10(1&2):47-68.
Klugherz et al., "Gene delivery from a DNA controlled-release stent in porcine coronary arteries," *Nature Biotechnology*, 2000;18:1181-1184.
Klugherz et al., "Gene Delivery to Pig Coronary Arteries from Stents Carrying Antibody-Tethered Adenovirus," *Human Gene Therapy*, 2002;13:443-454.
Panetta et al., "A Tissue-Engineered Stent for Cell-Based Vascular Gene Transfer," *Human Gene Therapy*, 2002;13;433-441.

* cited by examiner

*Primary Examiner*—Ileana Popa
*Assistant Examiner*—Joseph Woitach
(74) *Attorney, Agent, or Firm*—Mueting, Raasch & Gebhardt, P.A.

(57) ABSTRACT

The present invention provides a medical device, and methods of preparing and using a medical device. The medical device has a surface including a biologically active agent therein. The methods are particularly useful for preparing, for example, coated stents having a biologically active agent within the coating.

26 Claims, 9 Drawing Sheets

MEDICAL DEVICE HAVING A SURFACE INCLUDING A BIOLOGICALLY ACTIVE AGENT THEREIN, AND METHODS

CROSS-REFERENCE TO RELATED APPLICATIONS

The present application claims the benefit of U.S. Provisional Application No. 60/574,739, filed on 27 May 2004, which is incorporated herein by reference in its entirety.

BACKGROUND

Medical devices that are capable of releasing biologically active agents are desirable in the art. Such medical devices include, for example, stents (e.g., radially expandable stents), grafts, catheters, guide wires, heart valves, bone implants, spinal implants, covered stents, microspheres, and the like, or combinations thereof, that are inserted in a body during use. Such devices that release biologically active agents are useful, for example, in treating or preventing adverse reactions or diseases that may result from, or be associated with, the use of the medical device in the body.

It is known in the art of fabricating medical devices to coat surfaces of the device with coating materials chosen to impart a variety of desirable properties to the device. For example, coatings that include biologically active agents have been applied to stents to provide for drug release and for biocompatibility. Preferably, a biologically active agent remains in a medical device coating during normal handling procedures, but is released from the coating at the desired rate after insertion into a body lumen. However, known medical devices are often difficult to fabricate and/or suffer from not releasing the biologically active agent at the desired rate and/or at the desired time.

Thus, new medical devices, and methods of preparing medical devices that are capable of controlling the release of biologically active agents from their surfaces are needed in the art.

SUMMARY OF THE INVENTION

In one aspect, the present invention provides medical devices and methods of preparing medical devices. In one embodiment, the method includes: providing a device including a porous exposed surface including a biologically active agent therein; and heating at least the porous exposed surface to at least partially collapse the porous surface and encapsulate the biologically active agent. Preferably, the porous exposed surface is a porous polymeric coating on a surface of the device. Optionally, heating completely collapses the porous polymeric coating.

In another embodiment, the method of preparing a medical device includes: coating a surface of a device with a porous polymeric coating; at least partially loading the porous polymeric coating with a biologically active agent; and heating at least the porous polymeric coating to at least partially collapse a surface of the porous polymeric coating and encapsulate the biologically active agent. Optionally, heating completely collapses the porous polymeric coating.

In another embodiment, the method of preparing a medical device includes: applying a coating composition including a polymer and a water soluble porogen to at least a portion of a surface of a device; removing at least a portion of the water soluble porogen to form a porous polymeric coating on at least a portion of the surface of the device; at least partially loading the porous polymeric coating with a biologically active agent; and heating at least the porous polymeric coating to at least partially collapse a surface of the porous polymeric coating and encapsulate the biologically active agent. Optionally, the coating composition further includes a solvent, and the method further includes removing at least a portion of the solvent during or after applying the coating composition. Preferably, heating includes heating in air at a temperature of about 30° C. to about 100° C., preferably for about 30 seconds to about 60 minutes. Optionally, heating completely collapses the porous polymeric coating.

In another aspect, the present invention provides a method of controlling the release rate of a biologically active agent from a polymeric coating. The method includes: providing a device including an exposed surface including a porous polymeric coating including a biologically active agent therein; and heating at least the porous polymeric coating to at least partially collapse a surface of the porous polymeric coating and encapsulate the biologically active agent to control the release rate of the biologically active agent from the exposed surface. Optionally, heating completely collapses the porous polymeric coating.

In another aspect, the present invention provides a medical device including a reformed exposed surface. The reformed exposed surface includes a biologically active agent encapsulated therein. Preferably, the reformed exposed surface includes a porous polymeric surface that has been reformed by heating in air at a temperature of at least about 5° C. above the $T_g$ of a polymer in the porous polymeric surface.

In another aspect, the present invention provides a medical device including a reformed polymeric coating on a surface of the device. The reformed polymeric coating includes a biologically active agent encapsulated therein. Preferably, the reformed polymeric coating includes a porous polymeric coating that has been reformed by heating in air at a temperature of at least about 5° C. above the $T_g$ of a polymer in the polymeric coating.

Methods disclosed in the present invention can be advantageous, for example, in encapsulating biologically active agents that are sensitive to solvents (e.g., DNA that is denatured in solvents) in polymeric coatings. Further, such biologically active agents can preferably be loaded at high levels in the polymeric coatings. Moreover, presently disclosed conditions to encapsulate biologically active agents can be advantageous for encapsulating drugs that are sensitive to harsher conditions (e.g., cells that can be destroyed at higher temperatures).

Definitions

As used herein, the terms "porous" and "porosity" refer to physical characteristics of a matrix having open spaces (e.g., pores), preferably with interconnecting channels. Useful delivery matrices for biologically active agents include microporous matrices (i.e., matrices having pores with a sub-micrometer dimension), macroporous matrices (i.e., matrices having pores with dimensions of from one micrometer to hundreds of micrometers), and combinations thereof.

As used herein, the term "biologically active agent" means any agent capable of eliciting a response in a biological system such as, for example, living cell(s), tissue(s), organ(s), and being(s). Biologically active agents can include natural and/or synthetic agents.

As used herein, the term "drug" means any therapeutic agent.

As used herein, a "reformed" surface or polymeric coating refers to a surface or polymeric coating that has been heat treated to alter the physical structure of the surface or coating. For example, the physical structure of certain porous materials disclosed in the present application may be altered by heat treatment to at least partially collapse the surface, or to completely collapse the porous material.

As used herein, to "at least partially collapse" a surface means to reduce the size of surface pores in a surface to reduce of eliminate porosity.

As used herein, to "completely collapse" a porous polymeric coating means to substantially remove or eliminate pores throughout the bulk of the polymeric coating.

As used herein, to "at least partially load" a porous coating with a biologically active agent means that at least a portion of the pores of the coating contain biologically active agent.

As used herein, the term "encapsulate" means to enclose or entrap a biologically active agent or drug in a matrix in such a way as to control the release of the agent or drug from the matrix.

BRIEF DESCRIPTION OF THE DRAWINGS

FIG. 12 includes three scanning electron micrographs that illustrate the increased porosity observed by using increased levels of citric acid in the coating solution used to prepare porous PLGA coated stents.

FIG. 13 includes five scanning electron micrographs that illustrate the decrease in surface porosity observed after heat treating a porous PCL coated stent in an oven at 50° C. for 3 minutes (FIG. 13A), 5 minutes (FIG. 13B), 10 minutes (FIG. 13C), 15 minutes (FIG. 13D), and 25 minutes (FIG. 13E).

DETAILED DESCRIPTION OF PREFERRED EMBODIMENTS

Medical devices of the present invention include a surface having a biologically active agent therein. The devices are useful for delivering the biologically active agent to desired tissue. Such medical devices include, for example, stents, grafts, catheters, guide wires, heart valves, bone implants, spinal implants, covered stents, microspheres, and combinations thereof.

Medical devices of the present invention can be prepared from devices having a porous exposed surface including a biologically active agent therein. Such medical devices may be prepared by heating at least the porous exposed surface, to at least partially collapse the porous surface, and encapsulate the biologically active agent. A reformed exposed surface may result from heat treatment of the porous exposed surface. When the porous exposed surface is a polymeric coating on a surface of the device, a reformed polymeric coating may result from heat treatment of the polymeric coating.

Devices having a porous exposed surface, in turn, can be conveniently prepared, for example, by coating a surface of a device with a porous polymeric coating. Such porous polymeric coatings can be prepared by suitable methods known in the art. Such methods include, for example, applying a composition that includes a polymer and a pore forming material (i.e., a porogen) to the device, followed by removal of the porogen to form a porous polymeric surface. Suitable porogens include, for example, volatile materials and soluble materials. Biologically active agents can then be loaded into the porous polymeric surface by any convenient means.

Coating compositions useful in preparing the porous surfaces recited herein generally include a polymer and a porogen. The coating compositions optionally include a solvent, particularly when the coating composition is applied to the device by methods including, for example, spray coating or dip coating.

Polymers useful for preparing the porous surfaces recited herein are generally organic polymers having a glass transition temperature ($T_g$) of no greater than 70° C.

Preferred polymers include, for example, polycaprolactone (PCL), poly(lactide-co-glycolide) (PLGA), polyvinyl acetate (PVAC), polyvinyl alcohol, copolymers of PCL-PLGA, PLGA-polyethylene glycol (PEG), PCL-PEG, poly L-lactic acid (PLLA)-PEG, cellulose acetate, polyvinylidene chloride (PVDC), polyvinylidene fluoride, polymethyl acrylate, polyhexyl acrylate, polymethyl methacrylate, polyethyl methacrylate, polyhexyl methacrylate, polybutylene methyl acrylate (PBMA), and combinations thereof.

Suitable porogens include materials that may be removed after the coating composition has been applied to the device. Preferred porogens include, for example, volatile materials and soluble materials, particularly, water soluble materials. Preferred water soluble materials include citric acid, ascorbic acid, vitamin E, and combinations thereof.

When desired, a solvent may be used to dissolve, disperse, or suspend the polymer and porogen for application of the coating composition to the device. Preferably, the solvent dissolves at least the polymer, and more preferably both the polymer and the porogen, at the concentration used to apply the coating composition. Optionally, mixtures of solvents can be used to dissolve both the polymer and porogen. Suitable solvents include, for example, tetrahydrofuran, methylene chloride, chloroform, methanol, trifluoroethanol, acetone, and combinations thereof.

Coating compostitions used in the present invention preferably include at least 10% by weight, more preferably at least 20% by weight, and most preferably at least 25% by weight polymer, based on the total weight of polymer and porogen. Coating compositions used in the present invention preferably include at most 90% by weight, more preferably at most 80% by weight, and most preferably at most 50% by weight polymer, based on the total weight of polymer and porogen.

Coating compositions used in the present invention preferably include at least 10% by weight, more preferably at least 20% by weight, and most preferably at least 50% by weight porogen, based on the total weight of polymer and porogen. Coating compositions used in the present invention preferably include at most 90% by weight, more preferably at most 80% by weight, and most preferably at most 75% by weight porogen, based on the total weight of polymer and porogen.

Coating compositions used in the present invention that include solvent preferably include at least 90% by weight, more preferably at least 92% by weight, and most preferably at least 94% by weight solvent, based on the total weight of polymer, porogen, and solvent in the coating composition. Coating compositions used in the present invention that include solvent preferably include at most 99% by weight, more preferably at most 98% by weight, and most preferably at most 96% by weight solvent, based on the total weight of polymer, porogen, and solvent in the coating composition.

Coating compositions used in the present invention may be applied to a device by any suitable method. Useful methods include, for example, spray coating, dip coating, painting, and combinations thereof.

If the coating composition includes a solvent, the coating composition is preferably dried after application to the device. Suitable drying methods include, for example, air drying, oven drying (e.g., typically at an air temperature of no greater than 50° C.), oven drying gas flow (e.g., an inert gas such as nitrogen), and combinations thereof.

Upon application of the coating composition to the device, and drying if desired, the porogen is removed to form the porous surface and/or porous polymeric coating. Water soluble porogens can be removed by contacting the surface of the coating with water. Preferably the coated surface is immersed in water at a temperature of from 20° C. to 37° C. for a time of 60 minutes to 24 hours.

Biologically active agents may be contacted with the porous surface of the device to load (i.e., incorporate) the biologically active agent at the desired level. Typically, the porous surface is immersed in a loading medium (e.g., a solution or dispersion of the biologically active agent in a liquid).

Generally, the resulting loading level depends on the concentration of the biologically active agent in the loading medium, the amount of vacuum applied, and the immersion time and temperature. Loading is typically conducted at a temperature of from 4° C. to 37° C. for a time of 5 minutes to 2 hours. Preferably a vacuum of from 100 mm Hg to 800 mm Hg is applied during the immersion process.

Preferred biologically active agents include drugs. Preferred drugs include, for example, Plasmid DNA, genes, antisense oligonucleotides and other antisense agents, peptides, proteins, protein analogs, siRNA, shRNA, miRNA, ribozymes, DNAzymes and other DNA based agents, viral and non-viral vectors, lyposomes, cells, stem cells, antineoplastic agents, antiproliferative agents, antithrombogenic agents, anticoagulant agents, antiplatelet agents, antibiotics, anti-inflammatory agents, antimitotic agents, immunosuppressants, growth factors, cytokines, hormones, and combinations thereof.

The biologically active agent is preferably dissolved or dispersed in a liquid to form a loading medium. Suitable liquids include, for example, water, saline, phosphate buffer saline (PBS), methanol, ethanol, 2-morpholinoethane-sulfonic acid (MES) buffer, cell culture media, serum albumin solutions, and combinations thereof. Preferably the loading medium includes at least 0.1% by weight biologically active agent, based on the total weight of the loading medium. Preferably the loading medium includes at most 20% by weight, more preferably at most 10% by weight, and most preferably at most 5% by weight biologically active agent, based on the total weight of the loading medium.

Loading levels of biologically active agent in the porous surface are preferably at least 5% by weight, and more preferably at least 10% by weight, based on the total weight of the dried polymeric coating. Loading levels of biologically active agent in the porous surface are preferably at most 40% by weight, more preferably at most 30% by weight, and most preferably at most 20% by weight, based on the total weight of the dried polymeric coating.

The biologically active agent can be encapsulated in the polymeric coating by heat treatment. Preferably, the heat treatment at least partially collapses a porous surface by reducing the size of surface pores in the surface to reduce or eliminate porosity. Optionally, the heat treatment completely collapses the porous polymeric coating by substantially removing or eliminating pores throughout the bulk of the polymeric coating. Thus, encapsulation can be used to control the release profile of a biologically active agent from the polymeric coating by selection of the heat treatment conditions.

Although specific conditions selected to encapsulate the biologically active agent will depend on the polymer used to prepare the porous surface, typical conditions include heating in air at a temperature of about 30° C. to about 100° C. for about 30 seconds to about 60 minutes. Preferably, the conditions include heating in air at a temperature of at least about 5° C. above the $T_g$ of the polymer in the polymeric coating. The ability to encapsulate biologically active agents under mild conditions (e.g., heating in air at a temperature of about 30° C. to about 100° C. for about 30 seconds to about 60 minutes) can be advantageous in encapsulating drugs that are sensitive to harsher conditions (e.g., cells that can be destroyed at higher temperatures).

Biologically active agents in the polymeric coating are preferably released when the surface of the polymeric coating is contacted with a body fluid. Typically, release of the biologically active agent occurs through diffusion of the biologically active agent through the polymeric coating, degradation of the polymeric coating, or combinations thereof.

Medical devices of the present invention can deliver a biologically active agent by positioning the polymeric coating of the device proximate a tissue to provide an interface between the polymeric coating and the tissue. The encapsulated biologically active agent is then delivered to the interface between the polymeric coating and the tissue, preferably by allowing a fluid, preferably a body fluid, to at least partially fill the interface between the polymeric coating and the tissue. Exemplary body fluids include, for example, blood, serum, plasma, cerebral fluid, spinal fluid, pericardial fluid, intracellular fluid, extracellular fluid, and combinations thereof.

For example, when the medical device is a radially expandable stent, the stent can deliver a biologically active agent to the interior of a body lumen. The stent can be transluminally introduced into a selected portion of the body lumen, and at least a portion of the stent can be radially expanded to contact the body lumen.

Such methods can be useful for modifying the cellular response of a tissue to a disease, injury, or foreign body. Preferably, the medical device can controllably release the biologically active agent as described in the examples herein.

The present invention is illustrated by the following examples. It is to be understood that the particular examples, materials, amounts, and procedures are to be interpreted broadly in accordance with the scope and spirit of the invention as set forth herein.

EXAMPLES

Materials and Methods

Stainless steel stents were available under the trade designation S670 from Medtronic AVE (Santa Rosa, Calif.). An ultrasonic cleaner available under the trade designation BRANSON Model 2510 from (Branson Ultrasonic Corp., Danbury, Conn.) was used for cleaning the stents prior to coating. An model 8700-69 ultrasonic sprayer available from Sono-tek Corporation (MIlton, N.Y.) was used for spray coating stents. Citric acid was available as Cat. # C0759 from Sigma, St. Louis, Mo. Polycaprolactone (PCL) was available from available from Polymed Inc., Anderson, S.C. Poly(lactide-co-glycolide) (PLGA), 50/50 lactide/glycolide molar ratio, was available under the trade designation LACTEL BP-0100 from Birmingham Polymers, Inc., Birmingham, Ala. Plasmid DNA was available as Lot # PGB956 #346 from Valentis, Inc., Burlingame, Calif. Sterile phosphate buffer saline (PBS) was available from Hyclone (Logan, Utah). All other chemicals are available from Aldrich, Milwaukee, Wis., unless otherwise noted. All percentages are based on weight unless otherwise noted.

Example 1

Preparation of Stents Coated With Porous Polycaprolactone (PCL)

Stainless steel stents were twice cleaned in isopropanol (IPA) for 30 minutes each using an ultrasonic cleaner. The stents were then air dried and weighed. Stents were then sprayed with a thin coating of 2% by weight solution of PCL in THF to a coating weight of about 70-80 micrograms per stent using an ultrasonic sprayer. The coated stents were then annealed at 70° C. in an oven for about 0.5 hour to provide a stronger interface between the surface of the stainless steel stent and the PCL coating layer. The stronger interface may allow for better adhesion of subsequent layers of polymers sprayed onto the stent. After annealing, the stents were reweighed.

Figure 1:
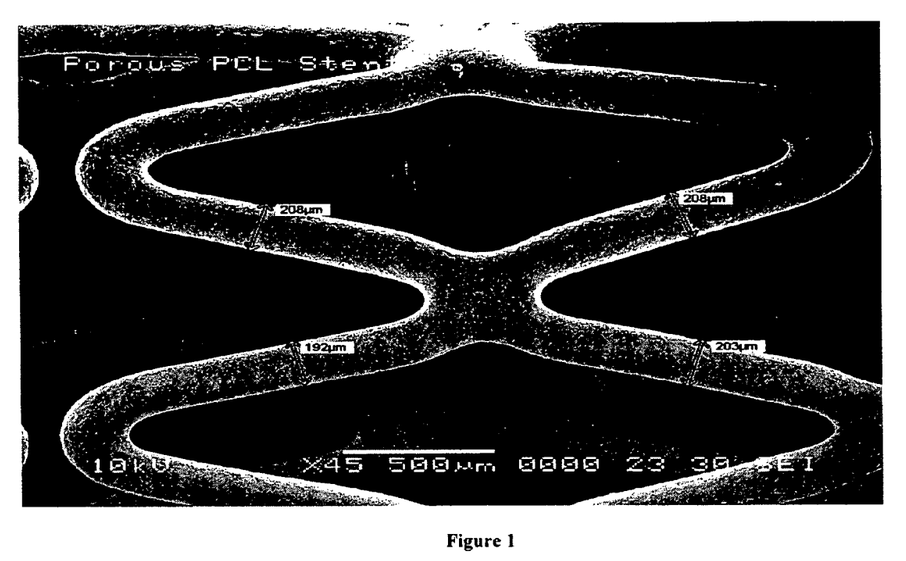
FIG. 1 is a scanning electron micrograph (at 45×) of a porous polycaprolactone (PCL) coated stent prepared using a 2% solids coating solution of 70 parts by weight citric acid/30 parts by weight PCL in THF.
Figure 2:
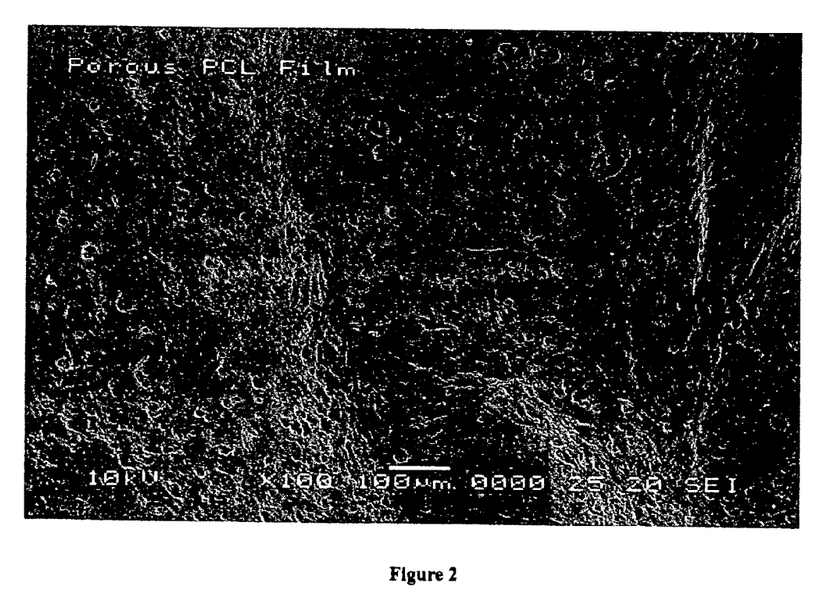
FIG. 2 is a scanning electron micrograph of the surface (at 100×) of the porous PCL coating of the coated stent as shown in FIG. 1.
Figure 3:
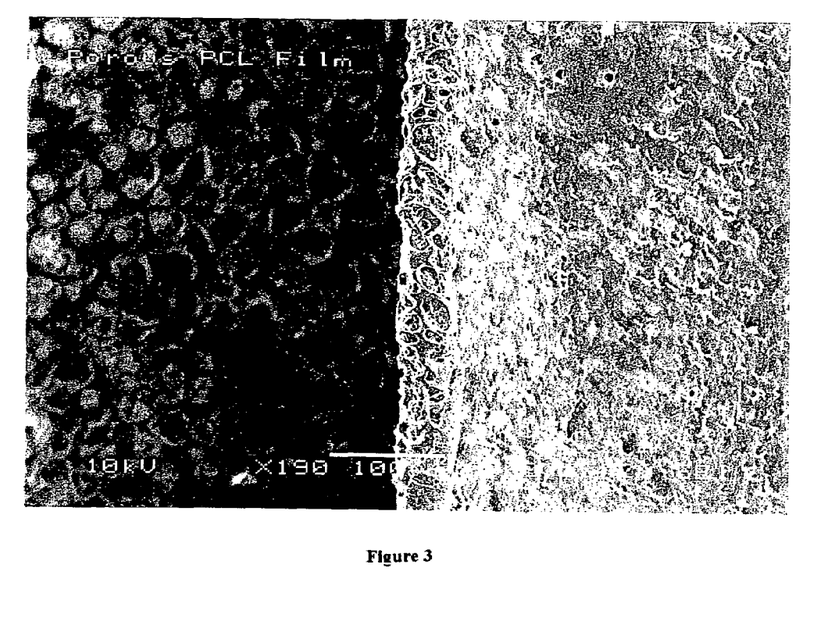
FIG. 3 is a scanning electron micrograph (at 190×) of a cross section of the porous PCL coating of the coated stent as shown in FIG. 1.

The coated surface of a stent was then sprayed with a 2% solution of 70% citric acid/30% PCL w/w in tetrahydrofuran (THF). The total mass of the dried coating was about 4 mg including the citric acid. The citric acid was then removed from the PCL layer by immersing the stent in a large amount of sterile water at 37° C. overnight, to provide a porous PCL coated stent that was then vacuum dried at room temperature, followed by weighing prior to drug loading. A picture of a porous PCL coated stent is shown in FIG. 1. Scanning electron micrographs (SEM) of porous PCL coatings, which confirm the porous nature of the PCL coatings, are shown in FIGS. 2 and 3.

Example 2

Heat Treatment or Heat Encapsulation of the Porous PCL Stent

Figure 4:
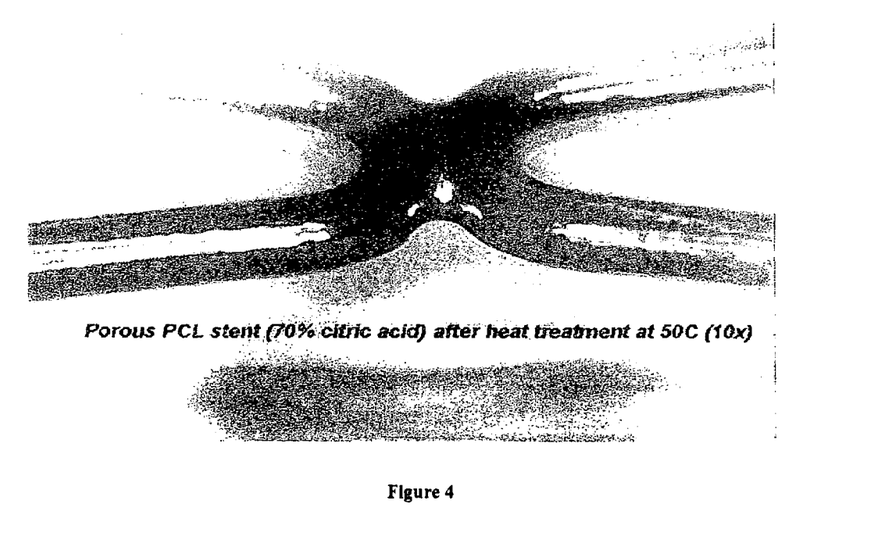
FIG. 4 is a picture (at 10×) of a porous PCL coated stent similar to that shown in FIG. 1 that has been heat treated in an oven at 50-55° C. for 0.5 hour.

A porous PCL coated stent, prepared as in Example 1, was placed inside a clean glass vial, which was then heat treated by placing inside an oven at 50-55° C. for about 0.5 hour. The heat treatment collapsed the porous structure observed in FIG. 1. If a drug is present within the pores, it will be encapsulated within the polymer matrix. The polymer coating looked smooth and uniform after heat encapsulation without a drug present. After heat encapsulation, the coating thickness was reduced to a very thin coating that was estimated to be a few micrometers. A heat encapsulated PCL coated stent with no drug present is shown in FIG. 4.

Example 3

Preparation of Stents Coated With Porous poly(lactide-co-glycolide) (PLGA)

Stainless steel stents were twice cleaned in isopropanol (IPA) for 30 minutes each using an ultrasonic cleaner. The stents were then air dried and weighed. Stents were then sprayed with a thin coating of a 2% solution of PLGA (50/50) in THF (w/w) to a coating weight of about 50-70 micrograms per stent using an ultrasonic sprayer. The stents were then annealed at 70° C. in an oven for about 0.5 hour to provide a stronger interface between the surface of the stainless steel stent and the PLGA coating layer. The stronger interface may allow for better adhesion of subsequent layers of polymers sprayed onto the stent. After annealing, the stents were reweighed.

Figure 5:
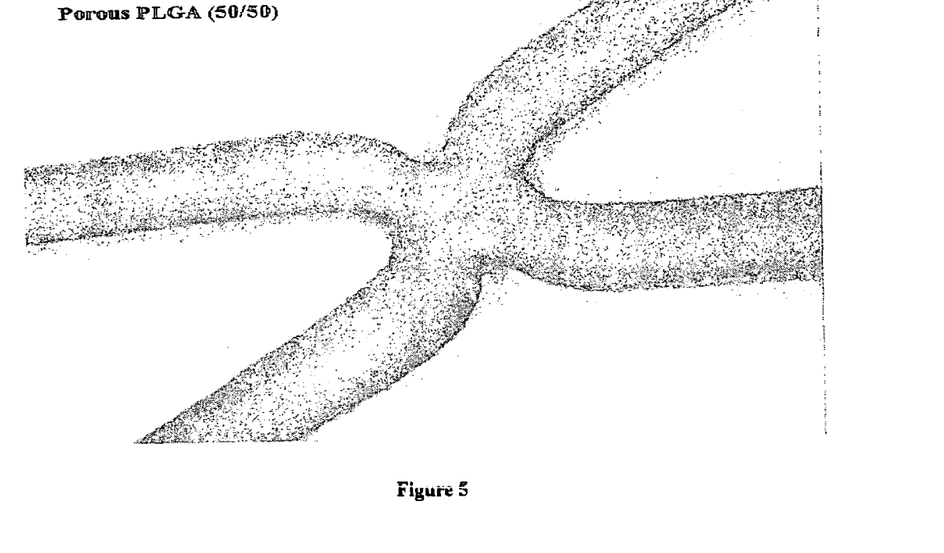
FIG. 5 is a picture (at 10×) of a porous PLGA coated stent prepared using a 2% solids coating solution of 70 parts by weight citric acid/30 parts by weight PLGA in THF.

The coated surface of a stent was then sprayed with a 2% solution of PLGA(50/50)/Citric acid in THF (70% citric acid/30% PLGA w/w). The total mass of the dried coating was about 4 mg including the citric acid. The citric acid was then removed from the PLGA layer by immersing the stent in a large amount of sterile water at 37° C. overnight, to provide a porous PLGA coated stent that was then vacuum dried at room temperature, followed by weighing prior to drug loading. A picture of a porous PLGA coated stent is shown in FIG. 5.

The coated surface of another stent was then sprayed with a 2% solution of PLGA(50/50)/Citric acid in THF (80% citric acid/20% PLGA w/w). The total mass of the dried coating was about 4 mg including the citric acid. The citric acid was then removed from the PLGA layer by immersing the stent in a large amount of sterile water at 37° C. overnight, to provide a porous PLGA coated stent that was then vacuum dried at room temperature, followed by weighing prior to drug loading.

Example 4

Loading and Encapsulating of Plasmid DNA into Porous PCL or PLGA Coated Stents

A porous PCL coated stent as prepared in Example 1, and illustrated in FIG. 1, was immersed in a small vial containing a plasmid DNA loading solution at a predetermined concentration of Plasmid DNA in 88% methanol/12% water (v/v). About 76 cm Hg Vacuum was then applied for 5-10 minutes to allow the DNA to permeate throughout the pores, after which the stent was removed from the DNA solution and dried under a clean biohood for about 2 hours. The stent was further vacuum dried at room temperature (i.e., about 20-22° C.) overnight and then weighed to determine the amount of loaded DNA. The encapsulation of plasmid DNA was carried out with DNA present in the pores of the porous PCL coating. The stent was placed in a clean glass vial and placed inside an oven for about 0.5 hour at 50-55° C. The heat softened the PCL coating and collapsed the porous structure, thus encapsulating the DNA within the PCL matrix.

Figure 6:
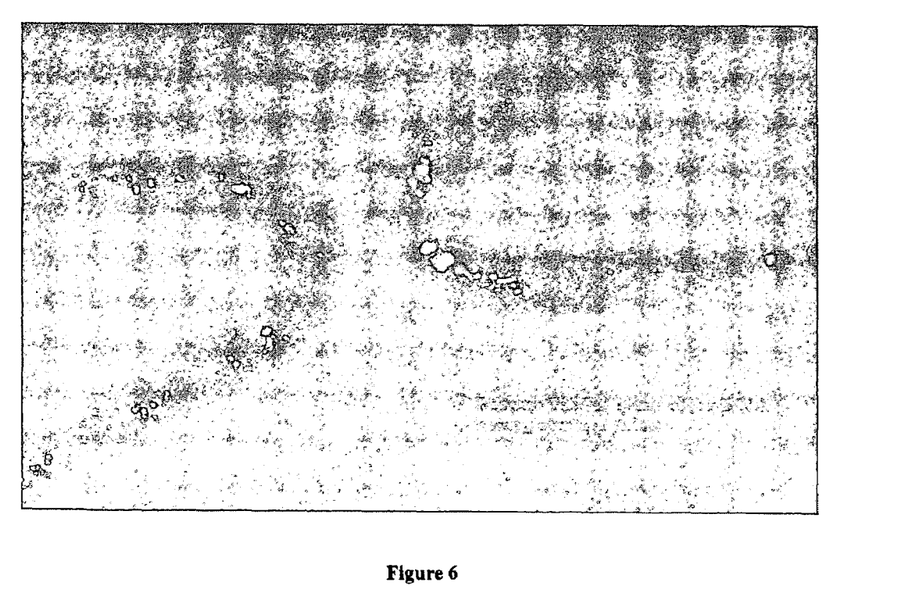
FIG. 6 is a picture (at 10×) of a porous PLGA coated stent similar to that shown in FIG. 5 that has been loaded with Plasmid DNA.
Figure 7:
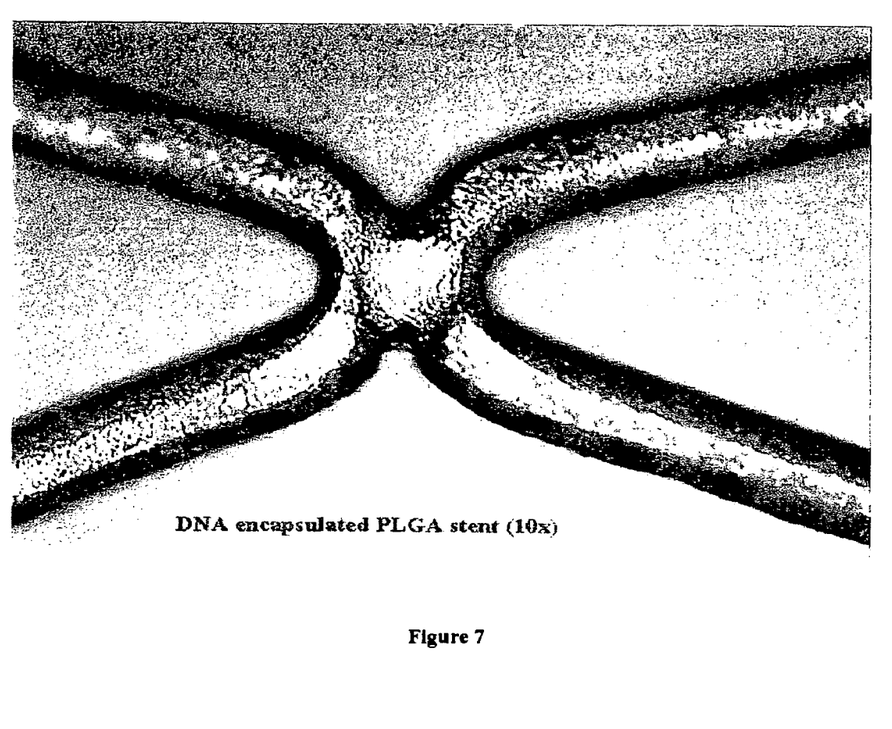
FIG. 7 is a picture (at 10×) of a Plasmid DNA loaded porous PLGA coated stent similar to that shown in FIG. 6 that has been heat treated in an oven at 65-70° C. for 0.5 hour to encapsulate the Plasmid DNA in the PLGA coating.

A porous PLGA coated stent as prepared in Example 3, and illustrated in FIG. 5, was immersed in a small vial containing a plasmid DNA loading solution at a predetermined concentration of Plasmid DNA in 88% methanol/12% water (v/v). About 76 cm Hg Vacuum was then applied for 5-10 minutes to allow the DNA to permeate throughout the pores, after which the stent was removed from the DNA solution and dried under a clean biohood for about 2 hours. The stent was further vacuum dried at room temperature (i.e., about 20-22° C.) overnight and then weighed to determine the amount of loaded DNA. The encapsulation of plasmid DNA was carried out with DNA present in the pores of the porous PLGA coating. The stent was placed in a clean glass vial and placed inside an oven for about 0.5 hour at 65-70° C. The heat softened the PLGA coating and collapsed the porous structure, thus encapsulating the DNA within a PLGA matrix. A porous PLGA coated stent loaded with Plasmid DNA is shown in FIG. 6, and a heat encapsulated Plasmid DNA in a PLGA coated stent is shown in FIG. 7. FIG. 7 shows that the porous structure in FIG. 6 has collapsed into a thin film with the Plasmid DNA encapsulated within.

Example 5

In Vitro Release Study of Plasmid DNA

Elution testing of DNA encapsulated PCL and PLGA coated stents was carried out in sterile PBS and at 37° C. Each stent was placed inside a sterile test tube and 2 ml of sterile PBS was added. The test tube was then placed horizontally in an incubator shaker at 37° C. and samples were withdrawn at regular time intervals and replaced with fresh sterile PBS. The samples were measured photometrically (UV-Vis) at a wavelength of 260 nanometers.

Figure 8:
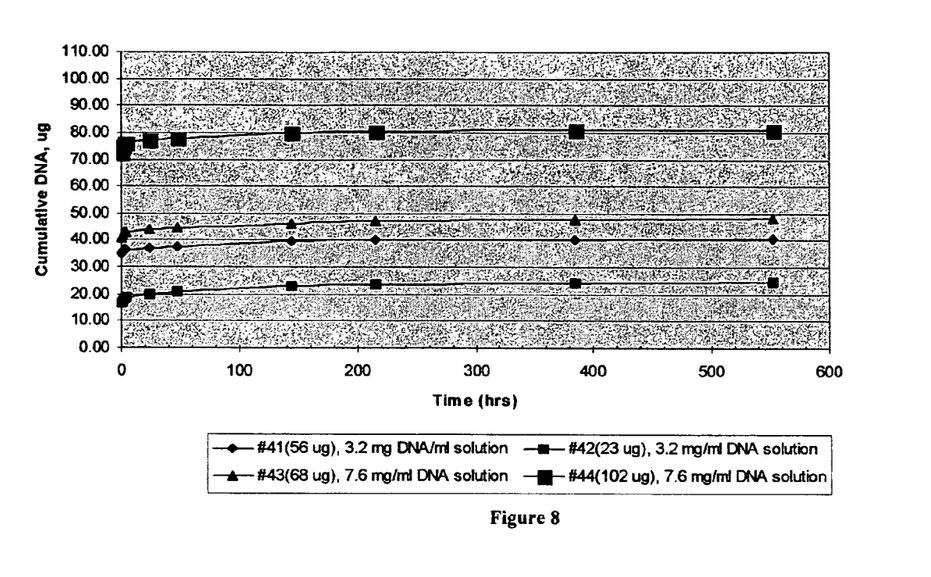
FIG. 8 is graphical representation of the measured levels of Plasmid DNA (y-axis, cumulative micrograms) released over time (x-axis, hours) in sterile PBS at 37° C. from a porous PCL coated stent (as described in Example 1) with encapsulated Plasmid DNA. The porous PCL coated stents were prepared using a 2% solids coating solution of 70 parts by weight citric acid/30 parts by weight PCL in THF. The plasmid DNA was loaded into the stents using a 3.2 mg DNA/ml solution to give 56 micrograms loading (#41, ♦) and 23 micrograms loading (#42, , ■); and using a 7.6 mg DNA/ml solution to give 68 micrograms loading (#43, ▲) and 102 micrograms loading (#44, ■). Stents #41 and #44 were subjected to 10 minutes of vacuum during loading, and stents #42 and #43 were subjected to 5 minutes of vacuum during loading. The Plasmid DNA loaded stents were heat treated in an oven at 50-55° C. for 0.5 hour to encapsulate the Plasmid DNA before release of Plasmid DNA in PBS was measured.

The release kinetics of Plasmid DNA from heat encapsulated porous PCL coated stents prepared using a 70% citric acid (pore former) formulation are shown in FIG. 8. The levels of released Plasmid DNA measured were higher for samples in which a plasmid DNA loading solution with a higher concentration of plasmid DNA was used in the Plasmid DNA loading procedure (as shown in FIG. 8 for samples #43 and 44 at 7.6 mg DNA/ml of loading solution) compared to when a plasmid DNA loading solution with a lower concentration of plasmid DNA was used (as shown in FIG. 8 for sample #41 and #42 at 3.2 mg DNA/ml of loading solution).

Figure 9:
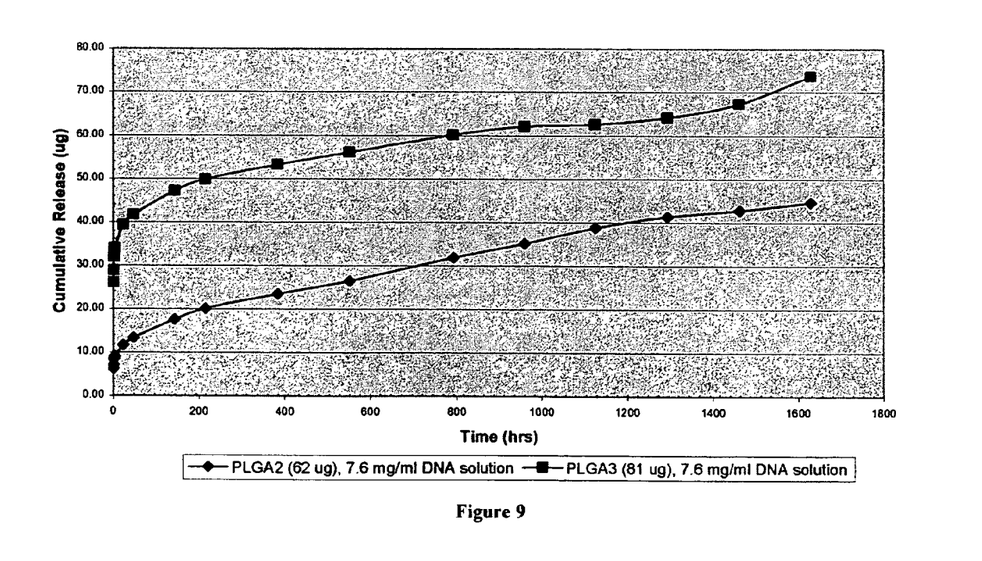
FIG. 9 is graphical representation of the measured levels of Plasmid DNA (y-axis, cumulative micrograms) released over time (x-axis, hours) in sterile PBS at 37° C. from an encapsulated Plasmid DNA, porous PLGA coated stent. The porous PLGA coated stents were prepared using a 2% solids coating solution of 80 parts by weight citric acid/20 parts by weight PLGA in THF. The plasmid DNA was loaded into the stents using a 7.6 mg DNA/ml solution to give 62 micrograms loading when subjected to 5 minutes of vacuum during loading (PLGA2, ♦), and 81 micrograms loading when subjected to 10 minutes of vacuum during loading (PLGA3, ■). The Plasmid DNA loaded stents were heat treated in an oven at 65-70° C. for 0.5 hour to encapsulate the Plasmid DNA before release of Plasmid DNA in PBS was measured.
Figure 10:
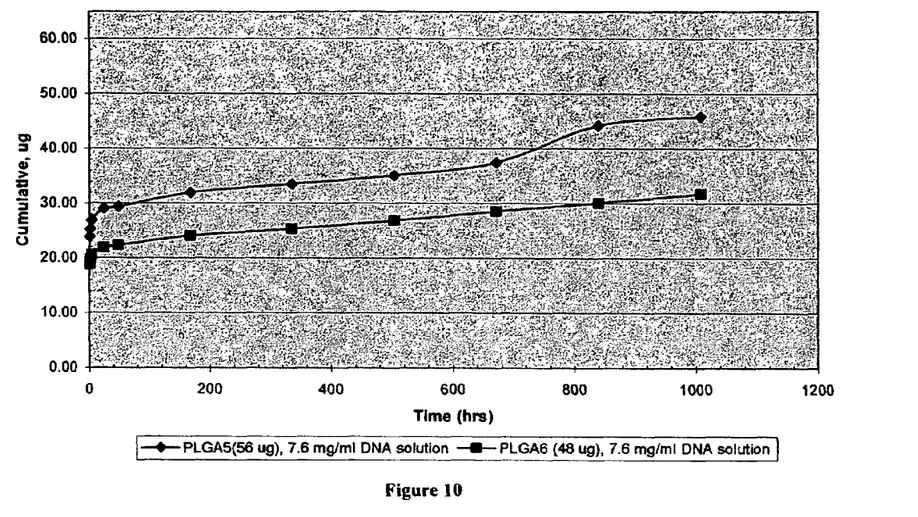
FIG. 10 is graphical representation of the measured levels of Plasmid DNA (y-axis, cumulative micrograms) released over time (x-axis, hours) in sterile PBS at 37° C. from an encapsulated Plasmid DNA, porous PLGA coated stent. The porous PLGA coated stents were prepared using a 2% solids coating solution of 70 parts by weight citric acid/30 parts by weight PLGA in THF. The plasmid DNA was loaded into the stents using a 7.6 mg DNA/ml solution to give 62 micrograms loading when subjected to 5 minutes of vacuum during loading (PLGA2, ♦), and 81 micrograms loading when subjected to 10 minutes of vacuum during loading (PLGA3, ■). The Plasmid DNA loaded stents were heat treated in an oven at 65-70° C. for 0.5 hour to encapsulate the Plasmid DNA before release of Plasmid DNA in PBS was measured.
Figure 11:
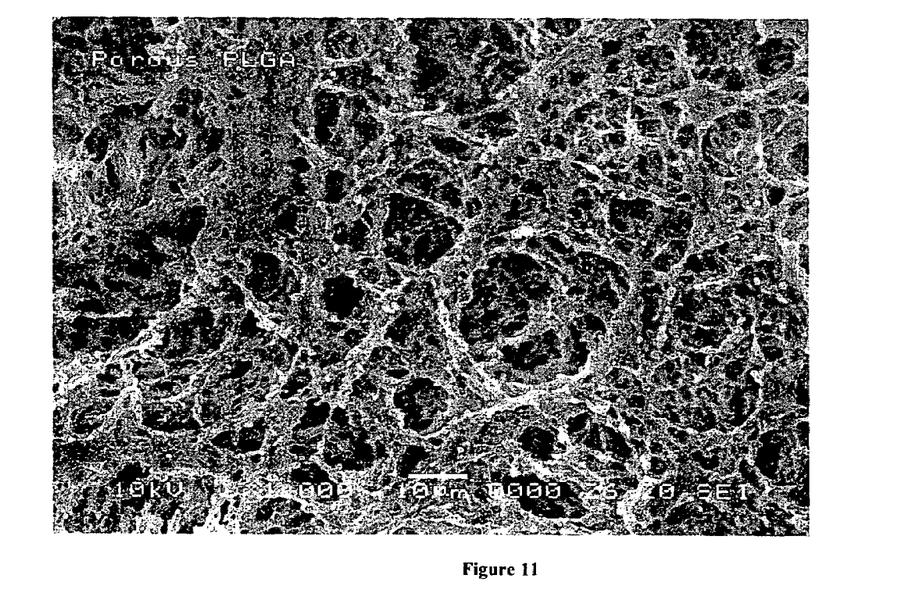
FIG. 11 is a scanning electron micrograph of the surface of a porous PLGA (at 1000×) coated stent prepared using a 2% solid coating solution of 80 parts by weight citric acid/20 parts by weight PLGA in THF.

The release kinetics of Plasmid DNA from heat encapsulated porous PLGA coated stents with 80% and 70% citric acid (pore former) are shown in FIGS. 9 and 10, respectively. The levels of released Plasmid DNA measured were higher for samples in which an 80% citric acid (pore former) formulation was used in the formation of the porous PLGA coating (samples PLGA2 and PLGA3) as compared to those of a 70% citric acid (pore former) formulation (samples PLGA5 and PLGA6), both using Plasmid DNA loading solutions with the same concentration of Plasmid DNA (7.6 mg/ml). This suggests that the PLGA matrix prepared using 80% citric acid is more porous than the PLGA matrix prepared using 70% citric acid, which may allow the Plasmid DNA to permeate better into the pores. A scanning electron micrograph (SEM) of the PLGA matrix prepared using 80% citric acid and 20% PLGA is shown in FIG. 11, which illustrates that when the percentage of the pore former (or porogen) increases, the resulting porosity of the matrix also increases.

The extended release profiles of these stents also indicated that DNA may be encapsulated deeply within the PLGA matrix.

Example 6

Figure 12A:
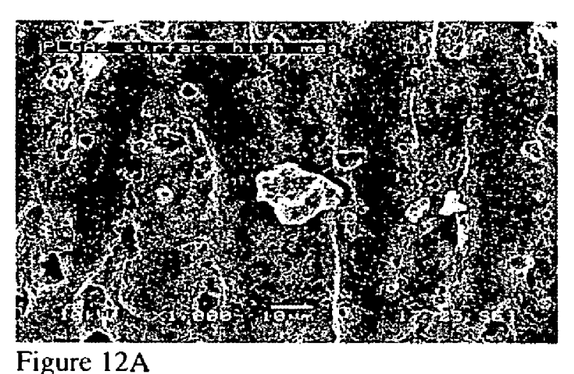
FIG. 12a is a scanning electron micrograph of a porous PLGA coating prepared using 30 parts citric acid/70 parts PLGA in the coating solution.
Figure 12B:
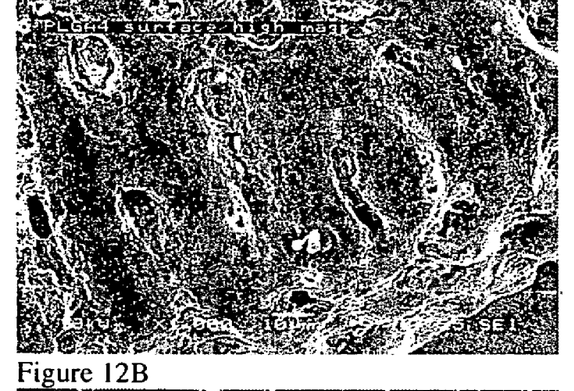
FIG. 12b is a scanning electron micrograph of a porous PLGA coating prepared using 50 parts citric acid/50 parts PLGA in the coating solution.
Figure 12C:
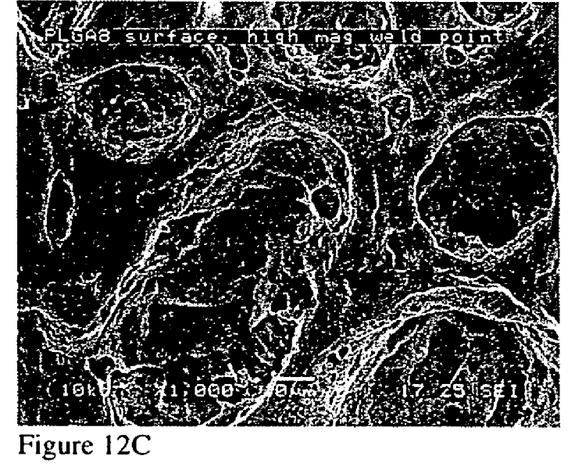
FIG. 12c is a scanning electron micrograph of a porous PLGA coating prepared using 75 parts citric acid/25 parts PLGA in the coating solution.
Figure 13A:
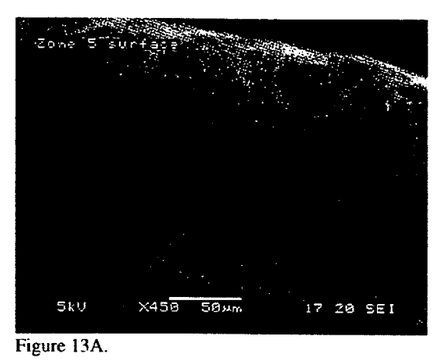
Figure 13B:
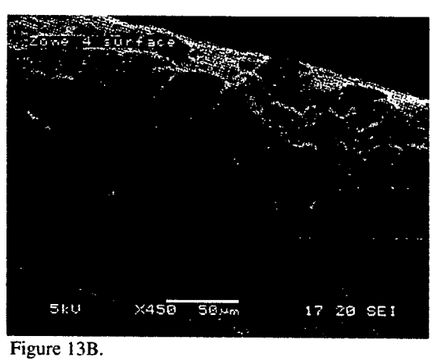
Figure 13C:
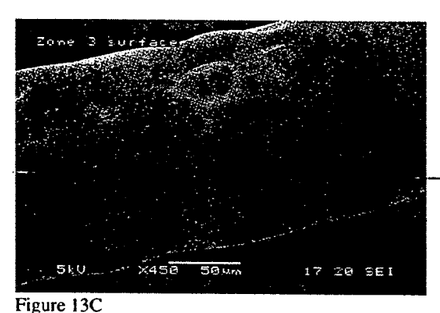
Figure 13D:
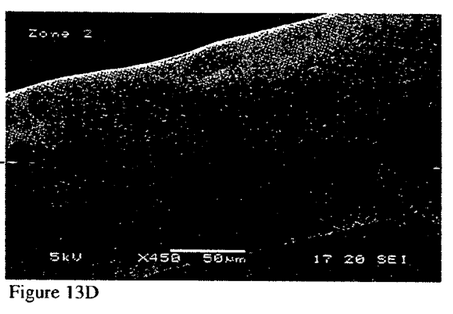
Figure 13E:
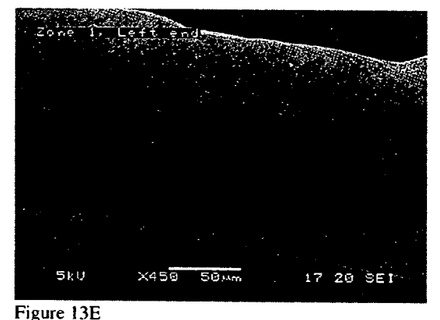

Porous PLGA coated stents were prepared as described in Example 3, except the concentration of citric acid (pore former) in the citric acid/PLGA coating solution was varied from 30% by weight to 75% by weight, based on the weight of coating solids. Scanning electron microscopy (SEM) of the porous coatings showed that the porosity or pore size of porous PLGA coated stents increased as the concentration of citric acid in the coating solution used in preparing the porous PLGA coated stents increased from 30% (FIG. 12A), to 50% (FIG. 12B), to 75% (FIG. 12C). Different porosities may allow drugs of various sizes and molecular weights to be incorporated into the porous matrix.

Example 7

Various sections of a porous PCL coated stent, prepared as described in Example 1, were placed in an oven at 50° C. At time intervals of 3, 5, 10, 15, and 25 minutes, a section was removed from the oven. The porosity of each section was examined by scanning electron microscopy (SEM). FIGS. 13A to 13E show the surface porosity of the coating after heat treatment at 3, 5, 10, 15 and 25 minutes, respectively. This example shows that various degrees of porosity can be achieved by selecting the duration of the heat treatment. The porosity of the coating can be used to vary the release rate and duration of release of drugs of varying sizes and types including, for example, proteins, genes, and peptides.

Example 8

Porous PLGA coated stents were prepared as described in Example 3, and were loaded with plasmid DNA in a manner similar to that described in Example 4, except that the stents were not subjected to heat encapsulation after being loaded with plasmid DNA.

Figure 14:
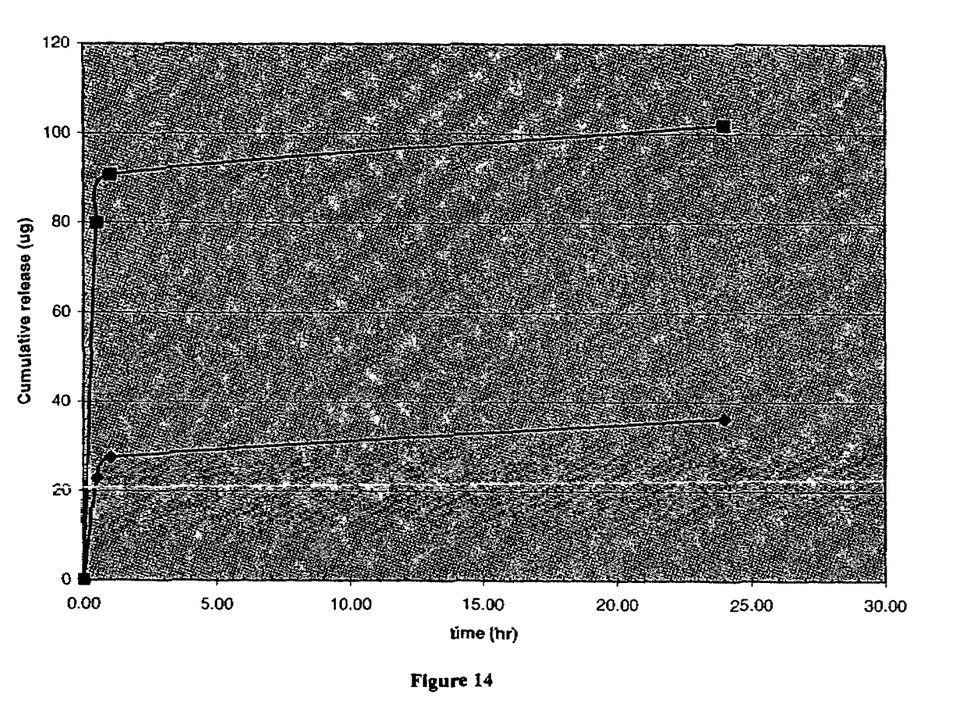
FIG. 14 is graphical representation of the measured levels of Plasmid DNA (y-axis, cumulative micrograms) released over time (x-axis, hours) in sterile PBS at 37° C. from a non-encapsulated Plasmid DNA, porous PLGA coated stent. The porous PLGA coated stents were prepared using a 2% solids coating solution of 70 parts by weight citric acid/30 parts by weight PLGA in THF. The plasmid DNA was loaded into the stents using a 7.4 mg DNA/ml solution to give 63 micrograms loading when subjected to 5 minutes of vacuum during loading (♦), and 140 micrograms loading when subjected to 10 minutes of vacuum during loading (■). The data suggests that samples which were subjected to longer times under vacuum during loading incorporated more biologically active agent or drug into the porous matrix.

Elution testing of these non-heat encapsulated, DNA loaded, porous PLGA coated stents was carried out in sterile PBS at 37° C. in a manner similar to that described in Example 5. The release kinetics of plasmid DNA from the non-heat encapsulated stents was compared to those of heat encapsulated (as shown in Example 5). The release kinetics of non-heat encapsulated stents is shown in FIG. 14. The two curves represent various amounts of drug loading using a 7.4 mg/ml Plasmid DNA solution and vacuum loading timing of about 5 and 10 minutes, respectively. The upper curve represents longer vacuum drug loading, which allows more time for the Plasmid DNA to permeate the porous matrix. As shown in Example 5 and FIG. 9, controlled release of plasmid DNA was achieved when the porous structure was collapsed and encapsulated the DNA within the PLGA. Conversely, the Plasmid DNA was released quickly from non-heat encapsulated, DNA loaded, porous PLGA coated stents (FIG. 14).

The complete disclosure of all patents, patent applications, and publications, and electronically available material (e.g., GenBank amino acid and nucleotide sequence submissions; and protein data bank (pdb) submissions) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of preparing a medical device comprising:
   providing a device comprising a porous exposed surface, wherein at least a portion of the pores contain a biologically active agent; and
   heating at least the porous exposed surface at a temperature of about 30° C. to about 100° C. to at least partially collapse the porous surface and encapsulate the biologically active agent.

2. The method of claim 1 wherein the porous exposed surface is a porous polymeric coating on a surface of the device.

3. The method of claim 2 wherein heating completely collapses the porous polymeric coating.

4. The method of claim 1 wherein the medical device is selected from the group consisting of stents, grafts, catheters, guide wires, heart valves, bone implants, spinal implants, covered stents, microspheres, and combinations thereof.

5. The method of claim 1 wherein the biologically active agent is a drug.

6. The method of claim 5 wherein the drug is selected from the group consisting of Plasmid DNA, genes, antisense oligonucleotides and other antisense agents, peptides, proteins, protein analogs, siRNA, shRNA, miRNA, ribozymes, DNAzymes and other DNA based agents, viral and non-viral vectors, lyposomes, cells, stem cells, antineoplastic agents, antiproliferative agents, antithrombogenic agents, anticoagulant agents, antiplatelet agents, antibiotics, anti-inflammatory agents, antimitotic agents, immunosuppressants, growth factors, cytokines, hormones, and combinations thereof.

7. A method of preparing a medical device comprising:
   coating a surface of a device with a porous polymeric coating;
   at least partially loading the porous polymeric coating with a biologically active agent; and
   heating at least the porous polymeric coating to at least partially collapse a surface of the porous polymeric coating and encapsulate the biologically active agent.

8. The method of claim 7 wherein heating completely collapses the porous polymeric coating.

9. The method of claim 7 wherein the medical device is selected from the group consisting of stents, grafts, catheters, guide wires, heart valves, bone implants, spinal implants, covered stents, microspheres, and combinations thereof.

10. The method of claim 7 wherein the biologically active agent is a drug.

11. The method of claim 10 wherein the drug is selected from the group consisting of Plasmid DNA, genes, antisense oligonucleotides and other antisense agents, peptides, proteins, protein analogs, siRNA, shRNA, miRNA, ribozymes, DNAzymes and other DNA based agents, viral and non-viral vectors, lyposomes, cells, stem cells, antineoplastic agents, antiproliferative agents, antithrombogenic agents, anticoagulant agents, antiplatelet agents, antibiotics, anti-inflammatory agents, antimitotic agents, immunosuppressants, growth factors, cytokines, hormones, and combinations thereof.

12. A method of preparing a medical device comprising:
   applying a coating composition comprising a polymer and a water soluble porogen to at least a portion of a surface of a device;
   removing at least a portion of the water soluble porogen to form a porous polymeric coating on at least a portion of the surface of the device;
   at least partially loading the porous polymeric coating with a biologically active agent; and heating at least the porous polymeric coating to at least partially collapse a surface of the porous polymeric coating and encapsulate the biologically active agent.

13. The method of claim 12 wherein the coating composition further comprises a solvent, and the method further includes removing at least a portion of the solvent during or after applying the coating composition.

14. The method of claim 12 wherein the polymer is selected from the group consisting of polycaprolactone (PCL), poly (lactide-co-glycolide) (PLGA), polyvinyl acetate (PVAC), polyvinyl alcohol, copolymers of PCL-PLGA, PLGA-polyethylene glycol (PEG), PCL-PEG, poly L-lactic acid (PLLA)-PEG, cellulose acetate, polyvinylidene chloride (PVDC), polyvinylidene fluoride, polymethyl acrylate, polyhexyl acrylate, polymethyl methacrylate, polyethyl methacrylate, polyhexyl methacrylate, polybutylene methyl acrylate (PBMA), and combinations thereof.

15. The method of claim 12 wherein the water soluble porogen is selected from the group consisting of citric acid, ascorbic acid, vitamin E, and combinations thereof.

16. The method of claim 12 wherein the medical device is selected from the group consisting of stents, grafts, catheters, guide wires, heart valves, bone implants, spinal implants, covered stents, microspheres, and combinations thereof.

17. The method of claim 12 wherein the biologically active agent is a drug.

18. The method of claim 17 wherein the drug is selected from the group consisting of Plasmid DNA, genes, antisense oligonucleotides and other antisense agents, peptides, proteins, protein analogs, siRNA, shRNA, miRNA, ribozymes, DNAzymes and other DNA based agents, viral and non-viral vectors, lyposomes, cells, stem cells, antineoplastic agents, antiproliferative agents, antithrombogenic agents, anticoagulant agents, antiplatelet agents, antibiotics, anti-inflammatory agents, antimitotic agents, immunosuppressants, growth factors, cytokines, hormones, and combinations thereof.

19. The method of claim 12 wherein heating comprises heating in air at a temperature of about 30° C. to about 100° C.

20. The method of claim 19 wherein heating comprises heating in air for about 30 seconds to about 60 minutes.

21. The method of claim 12 wherein heating completely collapses the porous polymeric coating.

22. A method of controlling the release rate of a biologically active agent from a polymeric coating, the method comprising:
providing a device comprising an exposed surface comprising a porous polymeric coating, wherein at least a portion of the pores contain a biologically active agent; and
heating at least the porous polymeric coating at a temperature of about 30° C. to about 100° C. to at least partially collapse a surface of the porous polymeric coating and encapsulate the biologically active agent to control the release rate of the biologically active agent from the exposed surface.

23. The method of claim 22 wherein heating completely collapses the porous polymeric coating.

24. The method of claim 22 wherein the device is selected from the group consisting of stents, grafts, catheters, guide wires, heart valves, bone implants, spinal implants, covered stents, microspheres, and combinations thereof.

25. The method of claim 22 wherein the biologically active agent is a drug.

26. The method of claim 25 wherein the drug is selected from the group consisting of Plasmid DNA, genes, antisense oligonucleotides and other antisense agents, peptides, proteins, protein analogs, siRNA, shRNA, miRNA, ribozymes, DNAzymes and other DNA based agents, viral and non-viral vectors, lyposomes, cells, stem cells, antineoplastic agents, antiproliferative agents, antithrombogenic agents, anticoagulant agents, antiplatelet agents, antibiotics, anti-inflammatory agents, antimitotic agents, immunosuppressants, growth factors, cytokines, hormones, and combinations thereof.

* * * * *